(12) United States Patent
Matson

(10) Patent No.: US 7,214,486 B2
(45) Date of Patent: *May 8, 2007

(54) DETECTION OF DNA DAMAGE

(75) Inventor: Wayne Matson, Ayer, MA (US)

(73) Assignee: ESA Biosciences, Inc., Chelmsford, MA (US)

( * ) Notice: Subject to any disclaimer, the term of this patent is extended or adjusted under 35 U.S.C. 154(b) by 347 days.

This patent is subject to a terminal disclaimer.

(21) Appl. No.: 10/366,909

(22) Filed: Feb. 14, 2003

(65) Prior Publication Data

US 2003/0180772 A1 Sep. 25, 2003

Related U.S. Application Data

(62) Division of application No. 09/687,047, filed on Oct. 13, 2000, now Pat. No. 6,548,252.

(51) Int. Cl.
*C12Q 1/68* (2006.01)
(52) U.S. Cl. .......................................... 435/6
(58) Field of Classification Search ...................... 435/6
See application file for complete search history.

(56) References Cited

U.S. PATENT DOCUMENTS

| | | | |
|---|---|---|---|
| 5,104,639 A | 4/1992 | Matson | 424/2 |
| 6,096,556 A | 8/2000 | Heinecke | 436/89 |
| 6,268,220 B1 * | 7/2001 | Heinecke | 436/501 |
| 6,410,274 B1 | 6/2002 | Bhikhabhai | 435/91.1 |
| 6,544,734 B1 | 4/2003 | Briscoe et al. | 435/6 |
| 6,548,252 B1 | 4/2003 | Matson | 435/6 |

FOREIGN PATENT DOCUMENTS

| | | |
|---|---|---|
| WO | WO 97/27327 | 7/1997 |
| WO | PCT/US98/22275 | 10/1998 |
| WO | WO 98/10294 | 12/1998 |

OTHER PUBLICATIONS

Hazen et al. 3-chlorotyrosine, a specific marker of myeloperoxidase-catalyzed oxidation, is markedly elevated in low density lipoprotein isolated from human antherosclerotic intima. Journal of clinical investigation, vol. 99, No. 9, pp. 2075-2081.*
Kasai H. Analysis of a form of oxidative DNA damage, 8-hydroxy-2'deoxyguanosine, as a marker of cellular oxidative stress during carcinogenesis. Mutation Research, vol. 387, pp. 147-163, Dec. 1997.*
Hurst, The Journal of Clinical Investigation, vol. 109, pp. 127-1289, 2002.*
Van-der Vliet et al. American Journal of Physiology-Lung Cellular and Molecular Physiology, vol. 279, pp. L537-L546, Sep. 2000.*
Hensley et al. Journal of High Resolution Chromatography, vol. 22, pp. 429-437, 1999.*
Foksinski et al., "Oxidative DNA base damage in cancerous tissues of patients undergoing brachytherapy," Cancer Letters, 1998, vol. 169-173.*

"Urinary 8-hydroxy-2'-deoxyguanosine as a biological marker of in vivo oxidative DNA damage", Shigenaga et al., Proceedings of the National Academy of Sciences,USA, Dec. 1989, vol. 86, pp. 9697-9701.
"Assays of Oxidative DNA Damage Biomarkers 8-Oxo-2'-deoxyguanosine and 8-Oxoguanine in Nuclear DNA and Biological Fluids by High-Performance Liquid Chromatography with Electrochemical Detection", Shigenaga et al., Methods in Enzymology, 1994, vol. 234, pp. 16-33.
"A Carbon Column-Based Liquid Chromatography Electrochemical Approach to Routine 8-hydroxy-2'-Deoxyguanosine Measurements in Urine and other Biologic Matrices: A One-Year Evaluation of Methods", Bogdanov et al., *Free Radical Biology & Medicine*, vol. 27, Nos. 5/6, 1999, pp. 647-666.
"Continuous Separations with Microfabricated Electrophoresis—Electrochemical Array Detection", Gavin et al., *J. Am. Chem. Soc.*, 1996, 118, 8932-8936.
Stanley L. Hazen and Jay W. Heinecke "3-Chlorotyrosine, a Specific Marker of Myeloperoxidase-catalyzed Oxidation, is Markedly Elevated in Low Density Lipoprotein Isolated from Human Atherosclerotic Intima" Rapid Publication vol. 99, No. 9, May 1997, 2075-2081.
Hurst, The Journal of Clinical Investigation, vol. 109, pp. 127-1289, 2002.
Van-der Vliet et al., American Journal of Physiology-Lung Cellular and Molecular Physiology, vol. 279, pp. L537-L546, Sep. 2000.
Hensley et al., Journal of High Resolution Chromatography,vol. 22, pp. 429-437, 1999.
Helbock, H. J. et al.: "8-Hydroxydeoxyguanosine and 8-hydroxyguanine as biomarkers of oxidative DNA damage." Methods in Enzymology, 1999, vol. 300, 1999, pp. 156-166.
Souliotis, V. L. et al.: "Measurement of 0-6 methylguanine-type adducts in DNA and 0-6 alkylguanine-DNA-Alkyltransferase repair activity in normal and neoplastic human tissues." Comparative Biochemistry and Physiology B, vol. 101, No. 1-2, 1992, pp. 269-275.
Bianchini, F. et al.: "Quantification of 7-methyldeoxyguanosine using Immunoaffinity purification and HPLC with electrochemical detection." Careinogenesis (Oxford), vol. 14, No. 8, 1993, pp. 1677-1682.
Whiteman, Matthew et al.: "Hypochlorus acid-induced DNA base modification: potentiation by nitrite: Biomarkers of DNA damage by reactive oxygen species." Biochemical and Biophysical Research Communications, vol. 257, No. 2, Apr. 13, 1999, pp. 572-576.
Yu, Fei et al.: "Room temperature derivatization of 5-hydroxy-2'-deoxycytidine and 5?hydroxymethyl-2'-deoxyuridine for analysis by GC/MS." Jan. 1999, Biomarkers, vol. 4, nr. 1, pp. 85-92.

(Continued)

*Primary Examiner*—Young J. Kim
(74) *Attorney, Agent, or Firm*—Hayes Soloway P.C.

(57) ABSTRACT

The health condition of a living organism is detected by electrochemically analyzing samples from selected areas of the body of said living organism for elevated free levels of nucleotide excision products resulting from DNA or RNA damage.

4 Claims, 6 Drawing Sheets

OTHER PUBLICATIONS

Petruzzelli, Stefano et al.: "Plasma 3-nitrotyrosine in cigarette smokers." American Journal of Respiratory and Critical Care Medicine, vol. 156, No. 6, Dec. 1997, pp. 1902-1907.

Zwingmann, Ivo H. et al.: "Analysis of oxidative DNA damage and HPRT mutant frequencies in cancer patients before and after radiotherapy." Dec. 17, 1999, Mutation Research, vol. 431, nr. 2, pp. 361-369.

Toyokuni, S. et al.: "Quantitative immunohistochemical determination of 8?hydroxy?2'-deoxyguanosine by a monoclonal antibody N45.1: Its application to ferric nitrilotriacetate-induced renal carcinogenesis model." 1997, Laboratory Investigation, United States and Canadian Academy of Pathology, Baltimore, US, pp. 365-374.

Lenton, Kevin J. et al.: "Glutathione and ascurbate are negatively currelated oxidative DNA damage in human lymphocytes." Apr. 1999. Carcinogenesis (Oxford). vol. 20. nr. 4. pp. 607-613.

Shuker, David E. G. et al.: "Urinary markers for measuring exposure to endogenous and exogenous alkylating agents and precursors." 1993. Environmental Health Perspectives, vol. 99, nr. 0, pp. 33-37, Symposium on Biomarkers in Human Cancer, Part II: Exposure Monitoring and Molecular Dosimetry; Kailua-Kona, Hawaii, USA; Oct. 26-Nov. 1, 1991.

Jenner, Andrew et al.: "Measurement of oxidative DNA damage by gas chromatography-mass spectrometry: Ethanethiol prevents artifactual generation of oxidized DNA bases." Apr. 15, 1998, Biochemical Journal. vol. 331, nr. 2, pp. 365-369.

Ohshima, H. et al.: "Formation of 8-nitroguanine in DNA by peroxynitrite: A possible marker for DNA damage Induced by reactive nitrogen species in inflamed tissues." Proceedings of the American Association for Cancer Research Annual Meeting, vol. 37, No. 0, 1996, p. 143, & 87th Annual Meeting of the American Association for Cancer Research; Washington, D.C., USA; Apr. 20-24, 1996.

Chung, Fung-Lung: "The prevention of lung cancer induced by a tobacco-specific carcinogen in rodents by green and black tea." Apr. 1999, Proceedings of the Society for Experimental Biology and Medicine, vol. 220, nr. 4, pp. 224-248, 2nd International Scientific Symposium on Tea and Human Health; Washington, D.C., USA; Sep. 14-15, 1998.

Shen, Zhongzhou et al.: "Activated leukocytes oxidatively damage DNA, RNA, and the nucleotide pool through halide-dependent formation of hydroxyl radical." Biochemistry, vol. 39, No. 18, May 9, 2000, pp. 5474-5482.

Kaur, Harparkash et al.: "Measurement of oxidized and methylated DNA bases by HPLC with electrochemical detection." Biochemical Journal, vol. 318, No. 1, 1996, pp. 21-23.

Gal, A. et al.: "Nitrotyrosine formation, apoptosis, and oxidative damage: Relationships to nitric oxide production in SJL mice bearing the RcsX tumor." Cancer Research, May 15, 1997, vol. 57, No. 10, pp. 1823-1828.

* cited by examiner

8OH2'dG levels in four typical normal PAP smear samples
(top is 200 pg/ml standard)

O6MG levels in two typical normal PAP smear samples
(top is 500 pg/ml standard)

Comparison of supernate and cell patterns from PAP smear sample.
Note: This illustrates one of the criteria for initially selecting tyramine (TYRA) as a normalizer.

DETECTION OF DNA DAMAGE

CROSS-REFERENCE TO RELATED APPLICATION

This application is a divisional application of U.S. application Ser. No. 09/687,047 filed Oct. 13, 2000, now U.S. Pat. No. 6,548,252.

FIELD OF THE INVENTION

The present invention relates to improvements in diagnostic techniques, and more particularly to diagnostic techniques for detecting and identifying DNA or RNA damage. The invention has particular utility in the detection of cervical cancer and will be described in connection with such utility, although other utilities are contemplated, as will be discussed below in detail, including detection of other cancers and other disease conditions, as well as health conditions brought out by exposure to environmental insults such as radiation, metals, smoke and solvents.

BACKGROUND OF THE INVENTION

The current gold standard for detecting cervical cancer in women is the so-called "PAP Smear." However, the reliability of PAP Smear testing, which relies upon a technician's observations, under the microscope, of cellular morphology, may be compromised by technician fatigue and/or subjectivity. Even very experienced technicians may misread a slide. If a false-positive is "called" or the slide results in an "uncertain" call, the physical may err on the side of the patient's safety, and call for a hysterectomy (uterus removal) or total hysterectomy (uterus and ovary removal). This results in the patient taking a lifetime dose of hormone replacement medications to keep the body in balance. Of course, the failure to identify "a pre-cancerous condition" could lead to an even more disastrous result to a patient.

OBJECT OF THE INVENTION

It is thus a primary object of the invention to overcome the aforesaid and other disadvantages of the prior art. Another object of the invention is to provide an analytical technique for detecting and diagnosing disease conditions, as well as health conditions due to exposure to environmental conditions, by detecting and identifying DNA or RNA damage markers. Another more object of the invention is to provide a reliable, totally objective analytical technique for detecting cancer.

BRIEF DESCRIPTION OF THE INVENTION

In order to effect the foregoing and other objects, the present invention provides an analytical technique for detecting cancer or other disease and/or health conditions based on measurement of free levels of nucleotide excision products resulting from DNA or RNA damage, such as 8OH2'dG—8 hydroxy 2'deoxyguanosine; O6MG—O-6-methylguanine; 2dG—2'deoxyguanosine; 7MG—7-methylguanine; 8NG—8-nitroguanine; 8OHG—8-hydroxyguanine; 8OH2'dA—8-hydroxy-2-deoxyadenosine; 8OHA—8-hydroxyadenine; 5OH2'dCy—5-hydroxy 2'deoxycytidine; 5OHU—5-hydroxyuracil; 3NT—3-nitrotyrosine; or 3CIT—3-chlorotyrosine in biological samples from selected areas of the body. More particularly, the present invention is based on the hypothesis that specific areas of the body are semi-isolated in-situ biochemical environments for nucleotide excision products such as 8OH2'dG or other nucleotide excision products, and that the levels of such free 8OH2'dG or other nucleotide excision products in the semi-isolated environment magnify the combined defects of DNA or RNA damage and repair mechanisms. By way of specific example, the effective damage and repair rate increases in DNA in cancer, or pre-cancerous cells, has been found to be magnified by accumulation in the extra-cellular matrix in selected areas of the body of 8OH2'dG. For example, as applied to cervicalcancer, the cervix has been found to be a semi-isolated in-situ biochemical environment which may be accessed through cervico vaginal lavage sampling. Thus, an objective analytical technique for determination of cervical cancer is provided.

BRIEF DESCRIPTION OF THE DRAWINGS

For a further understand of nature and objects of the present invention, presence should be had to the following detailed description taken in conjunction with the accompanying drawings wherein.

DETAILED DESCRIPTION OF THE PREFERRED EMBODIMENT OF THE INVENTION

Figure 1:
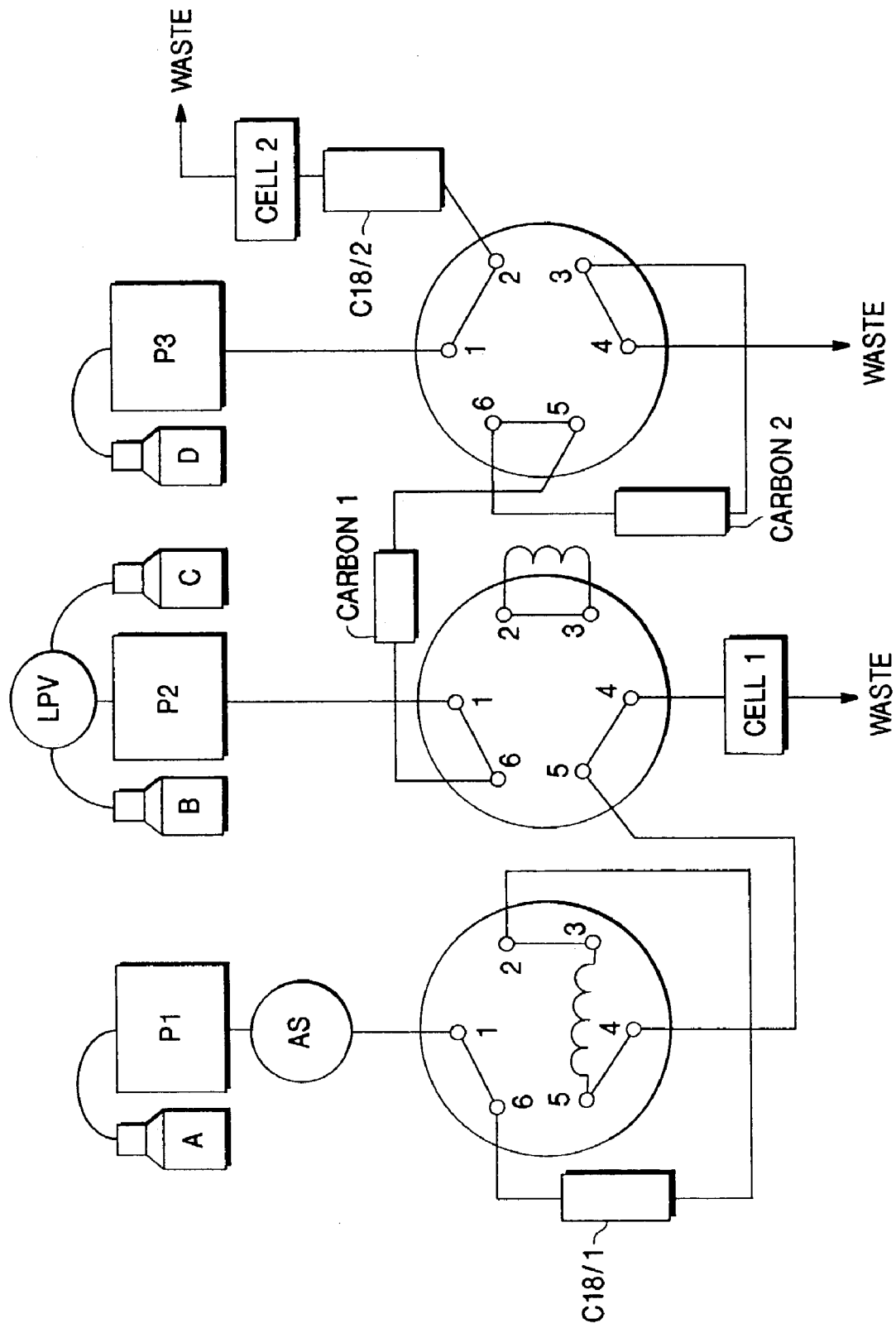
FIG. 1 is a schematic view of one form of sample separation and analysis system in accordance with the preferred embodiment of the invention.
Figure 2:
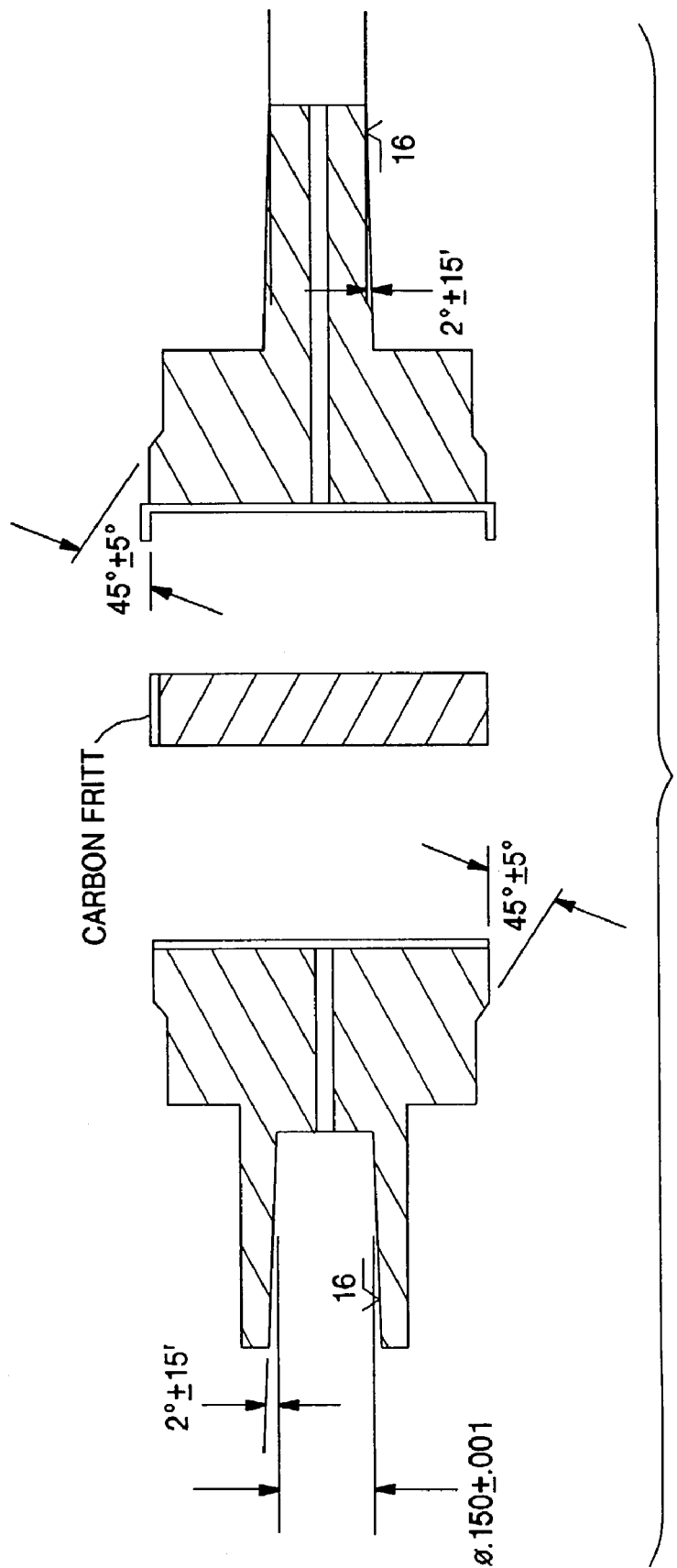
FIG. 2 is a side elevational view, in cross section, showing details of a preferred form of sample preparation column useful in accordance with a preferred embodiment of the present invention.
Figure 3:
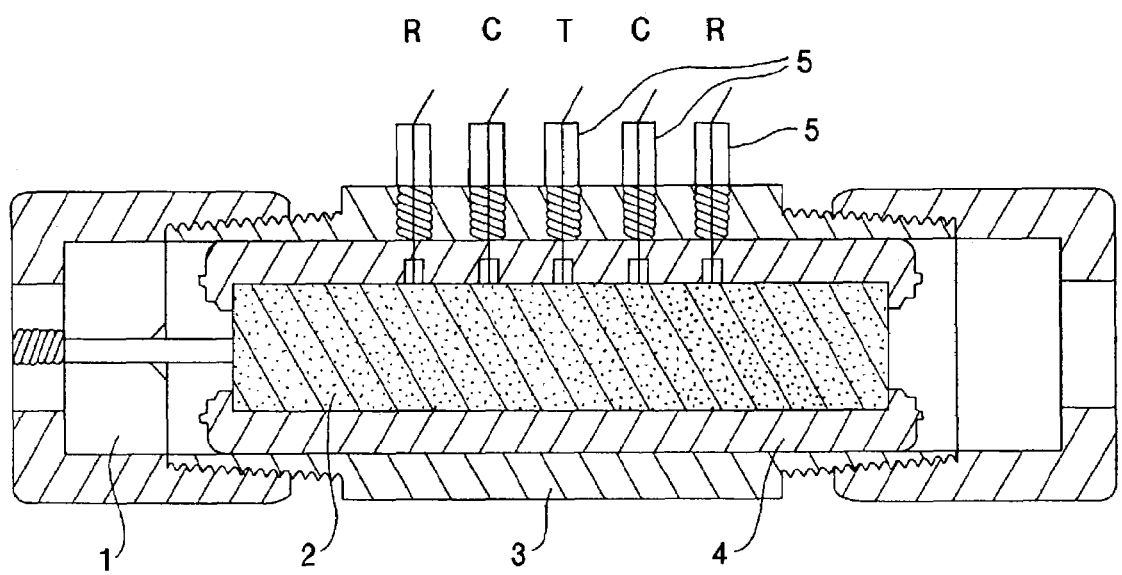
FIG. 3 is a side elevational view, in cross section, of a separation and/or testing column controlled as an electrochemical cell useful in accordance with a preferred embodiment of the invention.

Further understanding of the features and advantages of the present invention will be had from the following detailed description of the invention, which illustrates the electrochemical analysis of 8 hydroxy 2' deoxyguanosine (8OH2'dG) in cervico vaginal lavage or PAP smear swab samples. Analysis is accomplished using an electrochemical analytical system made in accordance with and following the general analytical procedures disclosed in PCT Application No. PCT/US98/22275, and as discussed in "A Carbon Column Based LCEC Approach to Routine 8-Hydroxy-2'-Doxyguanosine Measurements in Urine and Other Biological Matrices" (Bogdanov M B, et al. Free Rad. Ciol. Med. 27, 1227–1248, 1999).

The conventional hypothesis of hydroxyl radical DNA damage and repair and excretion of the hydroxylated adduct 8OH2'dG is that a hydroxyl radical reacts with the DNA causing hydroxylation of the deoxyguanosine at the 8 position. The damaged segment is then either excised by glycolysis as the 8Ohgua or by endonuclease excision as the 8OH2'dG5'monophosphate. The monophosphate is then dephosphorylated and the 8OH2'dG is rapidly excreted from the cell. The 8OH2'dG excreted to the extracellular matrix is then cleared rapidly from the body primarily via thp kidney and excretion in the urine. 8Ohgua can also be produced as a result of attack on RNA and glycolysis.

Studies performed with the technologies described above have confirmed certain basic elements of this hypothesis as follows:

1. Dialysis studies of 8OH2'dG in extracellular matrix with probes placed in brain and muscle of rat and mouse to measure the rate of production and excretion compared with the free levels inside the cellular material confirm that excretion from the cells is rapid. Similarly, comparison of CSF, Plasma and urinary levels of ca 1:10:2000 in ca 100 ALS and control subjects confirm that the rate of clearance from the body is high. Studies of saliva or sweat vs. urine levels and studies showing highly elevated levels in plasma kidney dialysis patients confirm that urinary excretion is the primary mode of removal.

2. Studies of urinary levels of 8OH2'dG within individuals over diurnal weekly, monthly and yearly intervals indicate that the rate of DNA damage and repair is highly constant and characteristic of an individual. Similarly, studies of siblings and parents which show a significantly closer agreement of sibling values indicate that the rate of DNA damage is strongly determined by genetic factors.

Other studies, however, have indicated some basic difficulties with the simplistic model of damage and repair which have relevance to the use of DNA damage markers as diagnostic tools.

1. The simple model of increased production of hydroxyl radical leading to increased DNA damage is incomplete.

Comparison of total body rate of production of hydroxyl radical estimated by salicylate spin trappings showed no correlation in normal individuals, ALS patients and Freidrich's Ataxia ("FA") patients of urine or plasma levels of 8OH2'dG. Nor was there any group elevation of total body hydroxyl radical production in FA or ALS although the 8OH2'dG levels were increased in CSF plasma or urine by 25–30%.

Urine levels of 8OH2'dG were significantly increased in individuals exposed to arsenic or o-toluidine or aniline although these materials play no direct role in the increase of hydroxyl radical production.

These studies suggest that conformational changes in DNA induced by exogenous or indogenous adducts or changes in sub cellular structures in proximity to DNA play a stronger role in increasing the rate of DNA damage than overall hydroxyl radial production. Also supporting this concept are studies I have performed showing no effect of simple antioxidants such as Ascorbate or Tocopherol on the levels of 8OH2'dG.

2. Relevant to the use of DNA damage rate measurements to cancer diagnosis I have observed that in *C. Elegans* culture there is a burst of 8OH2'dG production during the stage of rapid replication of the gonadal cells. In similar experiments I observed that a toxin (3 nitro propionic acid, 3NP) increased the rate of DNA damage during replication. When the toxin was removed after exposure the rate of damage was still maintained at a higher level indicating that the initiation of a higher rate of damage creates a biochemical state or feed back that persists beyond the time of the applied insult.

3. It has also been observed in human controls, ALS patients and FA patients and in *C. Elegans* culture that the levels of 8OH2'dG that remain in the DNA (measured by extracting and hydrolyzing the DNA) are only weekly correlated with the rate of output of the 8OH2'dG. This indicates that both damage and repair are up regulated simultaneously and thus that measures of the free levels of excised DNA damage product provide a much more robust indicator of disorder related DNA damage processes.

4. In situations where there is a high rate of damage and repair the conventional sequence of excision of the 8OH2'dG phosphate, dephosphorylation of the 8OH2'dG and excretion of the 8OH2'dG does not hold. In rapid cell replication in *C. Elegans*, in 3NP insulted *C. Elegans* and in Cervix cancer cells (as described below) the 8OH2'dG phosphates are directly excreted.

5. Sampling specific to the site of insult is of considerable importance. In studies of smoking related increases of urinary 8OH2'dG levels, I have found a statistically significant increase of only 11% in a cohort of ca 200 smokers vs. ca 300 control non-smokers. However, the free levels of 8OH2'dG in the, extra-cellular matrix from pharyngeal swabs of smokers vs. non-smokers are elevated by a factor of 3x–4x when normalized against the cellular metabolite of tyrosine, 4-hydroxy phenyl lactic acid.

The synthesis of these studies and observations leading to the approach to cancer diagnosis is as follows:

1. When a cell begins extensive abnormal replication the changes in the conformation of the DNA during mitosis make it more susceptible to free radial damage and both increase the levels of excised damage products and change the nature of those products.

2. Sample sites which are semi-isolated in situ from physiological transport and excretion, reflecting the extracellular matrix around the affected cells will show highly increased levels of the repair products relative to the damage products remaining.

3. Levels of the repair products can be normalized against other cellular metabolites that are excreted to the extracellular matrix from metabolic processes that are not materially affected by free radical damage.

WORKING EXAMPLES

Cervico vaginal lavage samples were centrifuged on acquisition to separate the exfoliated cells and the supernatant containing the extracellular matrix. PAP smear swabs were vortexed in a normal saline solution and centrifuged to separate the exfoliated cells and extracellular matrix.

Analysis for 8OH2'dG in supernatants was accomplished in accordance with the teachings of PCT/US98/22275 using electrode preparation and sample concentration protocol described in Bogdanov et al, supra. Analysis for 8OH2'dG phosphates was accomplished by treating a subaliquot of the supernatants with alkaline phosphatase following the last stage of the DNA hydrolysis protocol described in Boganov et al, and determination of the 8OH2'dG phosphate level by difference between the alkaline phosphatase treated and the non-treated aliquot. Chlorotyrosine measurements of subaliquots of the supernatant were made according to the teachings in PCT/US98/22275 following the protocols in Boganov et al.

The process for determining appropriate normalizers and markers of sample integrity was to prepare and analyze extracts of the supernate and cells from cervico vaginal lavage and PAP smear samples, plasma red blood cell and leucocyte samples, buccal cell samples and induced sputum samples following the procedures in Kristal et al "Simultaneous Analysis of the Majority of Low-Molecular Weight Redox-Active Compounds from Mitochondria," Anal. Biochem. 263, 18–25(1998). Typically 600 peaks of redox active compounds are isolated from such preparations. The various samples were compared against themselves and against authentic reference standard mixtures primarily to search for peaks or unknown compounds with the following characteristics:

1. The peaks should be unique to cervico vaginal lavage or PAP smear samples in order that it not be compromised by inclusion of other cellular or biological material inclusion.

2. The peaks should be present in the supernate and not in the cellular extracts or at significantly higher relative concentration than the cellular extract in order to reflect a similar high rate of excretion from the cells as 8OH2'dG.

Secondarily, the patterns of cervico vaginal lavage and PAP smear samples were compared against urine and blood samples to determine the level for compounds that are highly elevated in blood, e.g. glutathione and urine, e.g. uric acid such that levels of these compounds indicate contamination and effects on 8OH2'dG levels could be established.

Of 16 peaks in the patterns meeting the criteria 1 and 2 Tyramine was identified. The other 15 peaks meeting the criteria are currently of unknown structure although they are also candidates for normalization. Levels of uric acid and glutathione in cellular material and supernate from cervico vaginal lavage and PAP smear samples established levels of ca 1000 ng/ml of uric acid and 50,000 ng/ml of glutathione below which no measurable impact on the 8OH2'dG would be expected. A typical example of the comparison for known compounds among cell types is shown in Table 1.

The carbon column switching instrumentation and the array instrumentation were combined by placing an 8 channel series sensor on the output of the first analytical column of the carbon column switching apparatus and a second 8 channel series sensor on the output of the second analytical column of the carbon column switching apparatus. This allowed the simultaneous determination of the uric acid glutathione and tyramine on the output of the first analytical column and the carbon column trapping, elimination of interferences and detection of 8OH2'dG and Chlorotyrosine on the second analytical column.

Figure 4:
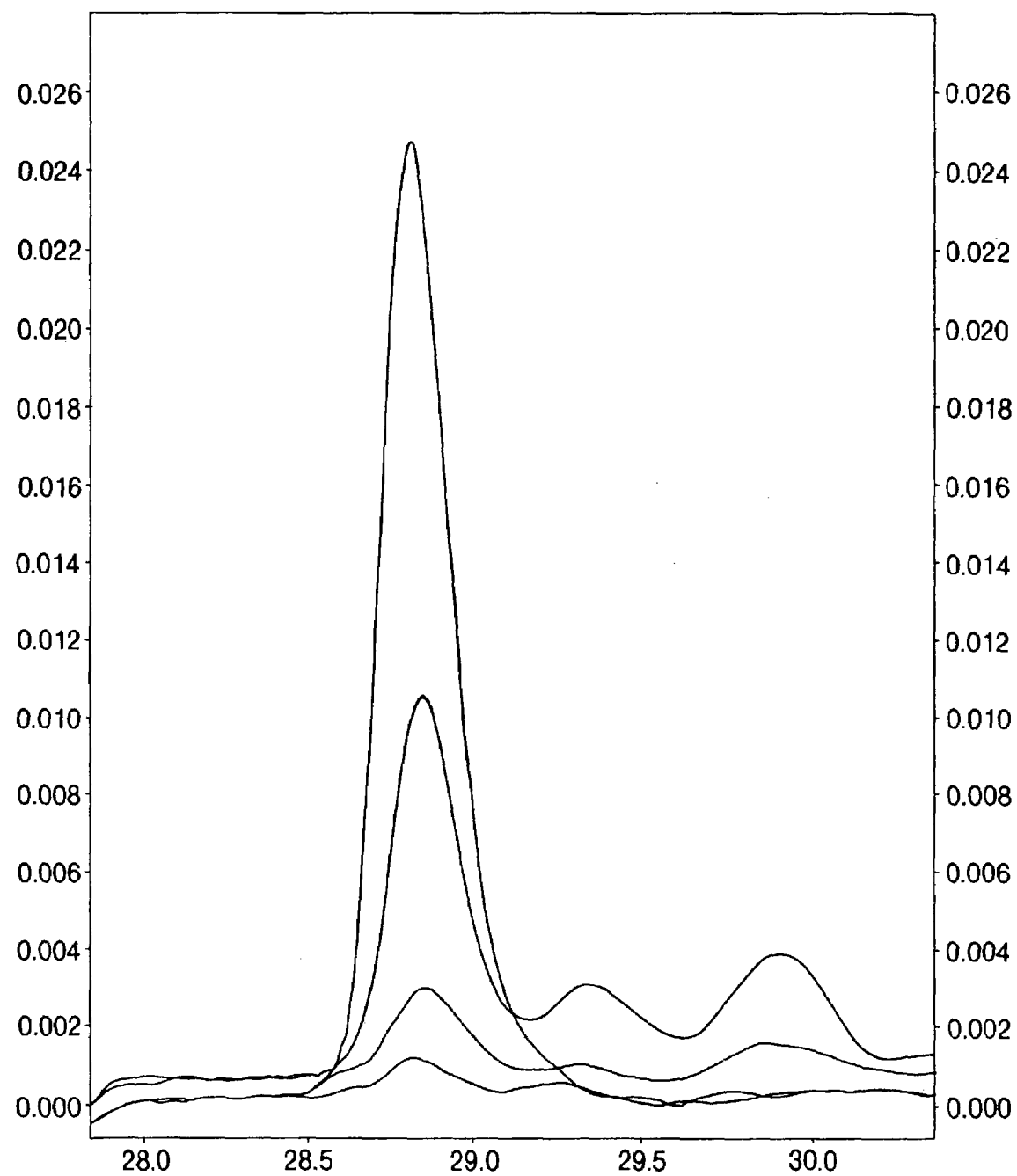
FIGS. 4 and 5 are a series of graphs showing the current over time of an electrochemical analysis for 8OH2'dG and O6MG, respectively, in cervico vaginal lavage samples in accordance with the present invention.
Figure 5:
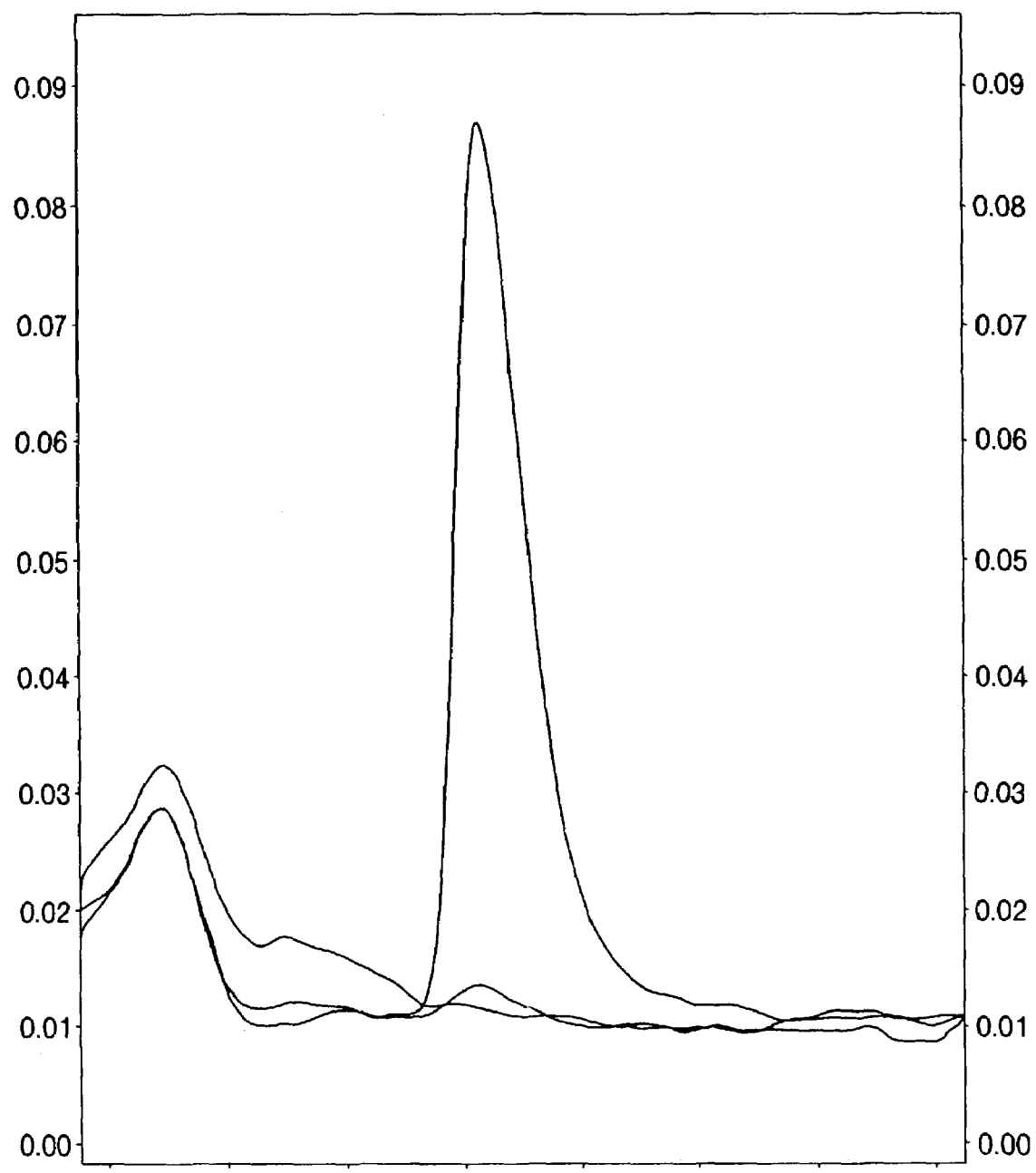

FIGS. 4 and 5 show typical responses for 8OH2'dG and O6MG in PAP smear samples. The figures illustrate the detection of 8OH2'dG in all samples and the limitation in detecting O6MG in some.

Figure 6:
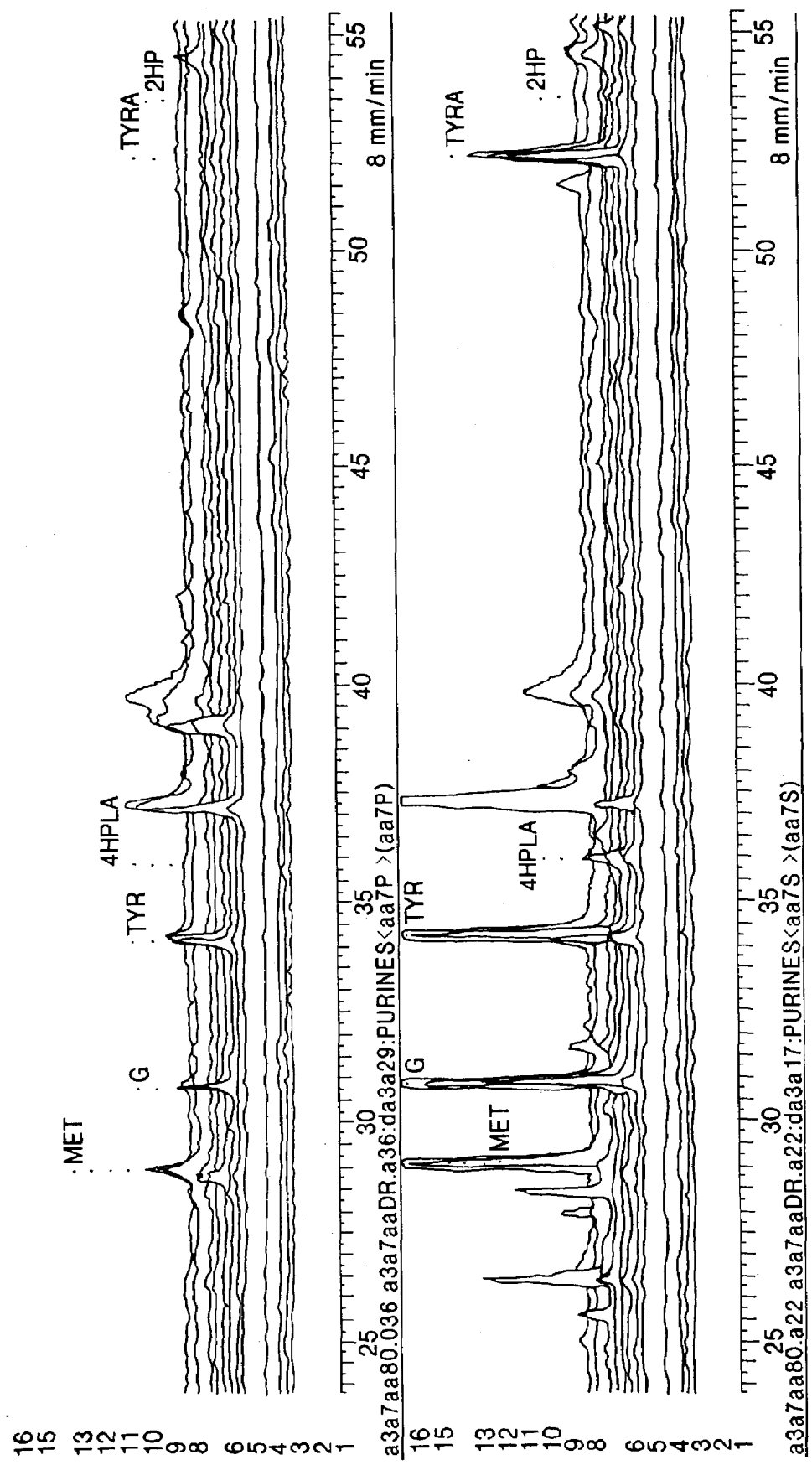
FIG. 6 are coulometric electrode array system patterns of PAP smear samples in accordance with the present invention.

FIG. 6 illustrates the CEAS patterns observed from cellular and supernatant preparations. These were compared against each other and against similar patterns of urine, plasma, whole blood and buccal cells to determine normalizing compounds and indicators of sample quality.

The results of the analytical protocols and concepts applied to 51 cervico vaginal lavage samples from 51 patients with various diagnoses and two normal PAP smear samples are shown in Table I.

Table II presents the data on 8OH2'dG, O6MG vs. an abbreviated diagnostic categorization ranked by tyramine divisor and sample weight or weight estimated from protein. CVL and PAP smear samples are ranked separately. Initial studies of vaginal vs. cervical swabs indicated higher levels of tyramine in the former. It is thus likely that tyramine is not an optimum normalizer since there are several other peaks that meet the criteria but have not been chemically identified. Table III presents preliminary data on relationships among free and DNA levels of 8OH2'dG, in the cervix and urine and plasma. There are some limitations on the data quality affecting interpretation. Precision on small samples (less than 2 mg) is only +/−220–30%. Storage histories are not completely documented and there are uncertainties associated with any study of a new matrix. However, some observations are indicated.

| CASE Compound ng/ml | 00000001.ora CL | 00000O03.ora BUC MUC | 00000006.ora BUC MUC | 00000008.ora BUC MUC | 00000009.ora CL | 00000014.ora BUG MUC | 00000016.ora CL | 00000017.ora CL | 00000024.ora CL | 00000029.ora BLOOD cal:15 | 00000033.ora CL |
|---|---|---|---|---|---|---|---|---|---|---|---|
| 2 HPAC | 0.13 | 0.63 | 0.40 | 0.20 | 0.09 | 0.25 | 0.62 | 0.24 | 294.78 | 3.23 | 1.96 |
| 3 MT | 0.20 | 0.19 | 0.18 | 0.08 | 0.12 | 0.17 | 0.11 | 0.22 | 1.39 | | 0.33 |
| 3 OHKY | 0.76 | 0.31 | 0.16 | 0.24 | 0.15 | 0.16 | 0.48 | | 0.65 | | 0.52 |
| 3 OMD | 0.26 | 0.31 | 0.39 | 0.44 | 0.32 | 0.39 | 0.51 | | 0.53 | 1.31 | 0.39 |
| 4 HBAC | | 0.44 | | 3.26 | 2.94 | 3.85 | 6.78 | 0.47 | 1.83 | 0.72 | 0.19 |
| 4 HPAC | 36.33 | 43.35 | 8.45 | 8.27 | 9.35 | 1.49 | 244.44 | 4.48 | 658.94 | 0.99 | 24.89 |
| 4 HPLA | 120.24 | 92.60 | 31.05 | 28.88 | 24.37 | 4.67 | 66.41 | 37.64 | 665.94 | 0.75 | 55.39 |
| 5 HIAA | 0.47 | 0.22 | 0.07 | 0.24 | 0.08 | 0.10 | 0.48 | | | 0.15 | 0.19 |
| 5 HT | 0.10 | | 0.11 | 0.19 | 1.13 | 0.11 | 0.26 | | | 0.79 | 0.19 |
| 5 HTP | 0.06 | 0.11 | 0.16 | | | 0.06 | 0.24 | 0.54 | 0.16 | | 0.13 |
| AM | 6.48 | 0.08 | 0.07 | | 0.06 | 0.25 | 1.70 | 0.11 | 13.69 | 0.11 | 0.40 |
| ASC | 0.62 | 0.13 | | 1011.01 | | 0.35 | 0.16 | 416.21 | 5.77 | 1.14 | 0.62 |
| CYS | 70.29 | 72.53 | 54.53 | 82.05 | 70.29 | 76.22 | 88.99 | 45.96 | 49.09 | 21.61 | 48.44 |
| DA | 21.93 | 6.66 | 0.94 | 3.27 | 14.19 | 1.25 | 2.01 | 0.38 | 3.33 | 0.43 | 0.41 |
| DOPAC | 0.11 | 0.11 | 0.12 | | 0.13 | 0.25 | 0.10 | | 1.40 | 0.37 | 0.22 |
| G | 12.52 | 8.62 | 3.44 | 237.98 | 19.46 | 3.63 | 61.18 | 89.06 | 1.38 | 1.27 | 86.94 |
| GR | 12.47 | 32.41 | 6.45 | 30.36 | 3.53 | 11.75 | 59.25 | 5.07 | 16.22 | 11.61 | 130.11 |
| GSSG | 3.10 | 111.76 | 25.78 | 24.08 | 42.70 | 37.48 | 193.42 | 27.37 | 2.12 | 1901.78 | 130.07 |
| HGA | 0.19 | 0.11 | 0.25 | | 0.14 | 0.16 | | 0.22 | 0.25 | 0.51 | 0.23 |
| HVA | 0.23 | 0.16 | 0.09 | 0.10 | 0.07 | 0.14 | 0.15 | 0.18 | 0.10 | 0.38 | 0.57 |
| HX | 24.75 | 39.98 | 8.10 | 619.81 | 48.07 | 74.60 | 461.74 | 152.57 | 2441.70 | 2445.10 | 112.92 |
| KYN | 1.03 | 0.09 | 24.39 | 1.63 | 0.29 | 0.07 | 5.09 | 0.48 | 28.95 | 0.30 | 9.74 |
| LD | 1.23 | 2.43 | 0.59 | 0.57 | 1.29 | 0.56 | 0.50 | 0.65 | 3.26 | 0.67 | 0.91 |
| MEL | 0.92 | 0.92 | 1.10 | 4.49 | 4.81 | 0.16 | 1.01 | 0.22 | 0.62 | 0.49 | 1.02 |
| MET | 42.88 | 0.82 | 4.21 | 441.49 | 43.94 | 1.27 | 454.70 | 39.17 | 73.65 | 831.72 | 677.84 |
| MHPG | 0.46 | 0.51 | 0.55 | 0.42 | 0.44 | 0.48 | 0.61 | | 0.95 | 0.66 | 0.40 |
| MN | 1.22 | 0.17 | 0.65 | 0.30 | 0.28 | 0.20 | 0.39 | 0.26 | 0.25 | 0.57 | 1.28 |
| NA5HT | 0.14 | 0.17 | 0.11 | 0.14 | 0.21 | 0.17 | 0.17 | | 0.18 | | 0.12 |
| NE | 0.40 | 0.10 | 0.33 | 0.19 | 0.36 | 0.26 | 0.32 | 0.26 | | | 0.22 |
| NMN | 0.30 | 0.51 | 0.28 | 0.32 | 0.49 | 0.29 | 0.50 | 0.37 | 0.34 | 0.32 | 3.30 |
| TPOL | 8.59 | 6.11 | 7.77 | 9.11 | 11.33 | 13.89 | 16.47 | 36.25 | 1.19 | 1.41 | 28.63 |
| TRP | 186.72 | 27.57 | 7.44 | 240.92 | 47.34 | 5.07 | 53.65 | 55.25 | 3904.06 | 523.63 | 237.29 |
| TRYPT | 0.15 | 1.19 | 0.61 | 0.83 | 82.32 | 0.43 | 8.19 | 0.74 | 13.85 | 0.50 | 277.00 |
| TYR | 266.00 | 551.51 | 251.17 | 717.54 | 98.95 | 140.30 | 214.95 | 227.17 | 7411.08 | 1545.97 | 639.34 |
| TYRA | 579.81 | 10.61 | 0.19 | 0.90 | 525.82 | 2.03 | 772.19 | 330.77 | 35.39 | 0.15 | 1088.90 |
| URIC | 695.51 | 703.83 | 3209.99 | 221.60 | 48.09 | 580.64 | 229.01 | 405.36 | 314.90 | 1992.77 | 371.60 |
| VMA | 0.44 | 0.43 | 0.12 | 0.26 | | 0.10 | 0.27 | 0.50 | 0.17 | | 1.12 |
| XAN | 73.44 | 235.05 | 16.67 | 107.60 | 16.00 | 53.93 | 1458.70 | 58.20 | 3669.12 | 343.39 | 45.54 |
| XANTHOSINE | 19.29 | 83.74 | 1.75 | 37.00 | 20.15 | 21.78 | 23.70 | 16.64 | 1461.96 | 151.37 | 34.65 |
| NORMALIZERS | | | | | | | | | | | |
| 8 OHdG pg/ml | 11.2 | 3.33 | 2.22 | 8.47 | 10.8 | 4.9 | 17.39 | 2.42 | 635.48 | 0.32 | 1.61 |
| 80 h/lyrx 100 | 4.21 | 0.60 | 0.80 | 1.10 | 10.91 | 3.49 | 8.09 | 1.07 | 8.57 | 0.02 | 0.25 |
| 8 oh/cysx 100 | 15.93 | 4.59 | 4.06 | 10.22 | 15.36 | 6.43 | 19.54 | 5.26 | 1273.76 | 1.48 | 3.32 |
| 8 oh/tyrax 1000 | 10.32 | 313.84 | 11684.21 | 9411.11 | 20.54 | 2413.79 | 22.52 | 7.32 | 17956.49 | 2133.33 | 1.48 |

TABLE II

| CASE CODE CVL. SAMPLES | 8 OH*1000/tyr | DIAG CODE | 8 OH pg/gm cal by protien | 8 OH/O6 MG |
|---|---|---|---|---|
| ESA006 | 17652.22 | C | 108934 | 0.12 |
| ESA041 | 5198.99 | C | 87132 | |
| ESA0447/21 | 3827.08 | C | 38897 | |
| ESA0447/16 | 3452.49 | C | 42132 | 0.24 |
| ESA051 | 2441.30 | C3 | 44150 | |
| ESA037 | 1881.84 | C3 | 31988 | |
| ESA011 | 1800.00 | C | NA | |
| ESA048 | 1373.63 | A, D, R | 12012 | |
| ESA033R3 | 940.82 | A, D, R | 18821 | 1.33 |
| ESA025CVL | 635.73 | A, R | 28812 | |
| ESA033R1 | 564.89 | A, R | 15168 | |
| ESA034 | 513.59 | A, D, R | 12997 | 0.92 |
| ESA030 | 513.55 | A, R | 19281 | |
| ESA043 | 510.68 | A, R | 12113 | 0.77 |
| ESA038 | 502.68 | A, R | 23881 | |
| ESA040 | 215.30 | A, R | NA | |
| ESA050 | 197.87 | A, R | 10687 | 1.92 |
| esa032s | 121.11 | A, D, R | 12188 | |
| esa029s | 74.25 | A, R | 2188 | |
| ESA035s | 38.50 | A, D, R | 1722 | |
| ESA018CVL | 35.74 | A, R | 21 | |
| ESA022CVL | 27.73 | A, R | 3324 | 1.01 |
| ESA004 | 22.53 | A, R | NA | |
| ESA019CVL | 22.05 | A, D, R | 922 | |
| ESA003 | 20.53 | AR | 1334 | |
| ESA023CVL | 20.49 | A, R | 1987 | |
| ESA001 | 19.31 | A, D, R | 1332 | |
| ESA039 | 15.53 | AR | 1435 | |
| ESA005 | 7.33 | A | 397 | |
| ESA036 | 3.79 | A | 433 | |
| esa027CVL | 2.91 | A | 198 | |
| ESA047 | 1.56 | N | 163 | GT10 |
| ESA012 | 1.48 | N | 289 | |
| ESA049 | 1.33 | N | 143 | |
| ESA020CVL | 0.71 | A | 208 | |
| esa031s | 0.71 | N | 134 | |
| ESA048 | 0.64 | N | 289 | |
| ESA021CVL | 0.81 | A | 189 | 7.44 |
| ESA042 | 0.57 | N | 215 | |
| ESA045 | 0.45 | N | 127 | GT10 |
| ESA026CVL | 0.36 | N | 131 | |
| ESA024CVL | 0.18 | N | 158 | |

| CASE CODE PAP SMEAR SAMPLES | 8 OH*1000/tyr | DIAG CODE | 8 OH pg/gm | 8 OH/O6MG |
|---|---|---|---|---|
| CON1R1 | 0.92 | N | 388 | 7.2 |
| CON2 | 1.03 | N | 442 | 11.2 |
| CON3 | 0.83 | N | 293 | 14.1 |
| CON4R1 | 0.72 | N | 528 | NA |
| CON1R5 | | | | |
| endo brush | 1.06 | N | 445 | 6.8 |
| exo brush | 0.94 | N | 502 | NA |
| vaginal pad1 | 0.12 | N | 28 | NA |
| CON5R1 | 2.44 | N | 308 | 11.1 |
| CON4R3 | 0.98 | N | 122 | 4.3 |
| CON5R3 | 1.87 | N | 354 | 7.5 |
| W001 | 2.19 | A, R | 125 | 1.25 |
| W002 | 4.1 | A, R | 507 | 0.73 |
| W003 | 58.28 | Hepatitis | 3855 | 0.57 |
| W004 | 8.23 | A, R | 200 | 0.58 |
| W005 | 2.19 | N | 75 | 1.58 |
| W006 | 4.3 | N, R | 500 | 0.84 |
| W007 | 2.1 | N | 90 | 0.71 |
| W008 | 27.49 | N, HPV | 361 | 0.55 |
| W009 | 113.04 | ?A, HPV | 1300 | 0.45 |
| W010 | 0.9 | 7A | 75 | 1.88 |
| W011 | 1.6 | N, R | 75 | 1.2 |
| W012 | 1.8 | N | 85 | 1.48 |
| W013 | 1.1 | N | 75 | 1.2 |
| W014 | 1.8 | N, R | 145 | 1.8 |
| W015 | 1.9 | N | 199 | 4.4 |
| W016 | 2.8 | N, R | 301 | 4.3 |
| W017 | 2.8 | A, R | 190 | 1.3 |
| W018 | 3.12 | A | 412 | 1.9 |

TABLE II-continued

| | | | | |
|---|---|---|---|---|
| W019 | 1.4 | N | 138 | 7.3 |
| W020 | 1.87 | A | 115 | 4.4 |
| W021 | 4.12 | N, R | 543 | 1.7 |
| W022 | 1.7 | A | 214 | GT10 |
| W023 | 56.9 | N, HPV | 3224 | 0.41 |
| W024 | 2.1 | A, R | 341 | 3 |
| W025 | 0.81 | N | 104 | NA |
| W026 | 2.3 | N, R | 122 | 5.7 |
| W027 | 2.8 | A, R | 107 | 4.4 |
| W028 | 1.6 | N | 115 | 8.1 |

N-normal PAP,
A-ASCUS,
C-cancer,
C3-CIN3,
D-dyaplasia,
R-vanos risk factors,
HPV-PCR+ viral ta
NA-not analysed, Interference

TABLE III

| URINE urine code | CVL SAMPLE 8 OH*1000/ tyra | URINE ug/gm 8 OH2'dG/creat | DNA pm/um 8 OH2'dG/ 2'dG | PLASMA pg/ml 8 OH2'DG |
|---|---|---|---|---|
| esa001u | | 3.15 | | |
| esa003u | | 4.97 | | |
| esa004u | | 4.57 | | |
| esa005u | 17652.22 | 14.48 | 5.81 | 31.90 |
| esa012u | 5198.99 | 3.30 | | 16.30 |
| esa006u | 2441.30 | 5.73 | | |
| esa018u | 1881.84 | 2.38 | 6.13 | 22.10 |
| esa019u | 1373.63 | 1.71 | | |
| esa020u | 940.82 | 4.11 | | |
| | 835.73 | 2.86 | 4.98 | 14.60 |
| esa022u | 564.89 | 3.94 | 5.87 | |
| esa023u | 513.59 | 1.79 | | |
| esa024u | 513.55 | 4.83 | | |
| esa025u | 510.66 | 2.19 | | |
| esa026u | 502.68 | 2.22 | | |
| esa027u | 215.30 | 5.38 | | |
| esa029u | 197.87 | 4.14 | | |
| esa030u | 121.11 | 2.16 | | |
| esa031u | 74.25 | 1.64 | | 11.80 |
| esa032u | 38.50 | 3.25 | | |
| esa033au | 35.74 | 3.05 | | |
| esa033bu | 27.73 | 2.40 | 3.44 | |
| esa034u | 22.53 | 2.15 | 3.38 | 15.30 |
| esa035u | 22.05 | 3.04 | | |
| esa036u | 20.53 | 5.53 | 5.12 | 16.40 |
| esa037 | 20.49 | 5.45 | 4.76 | |
| esa038u | 19.31 | 3.95 | | |
| esa039u | 15.53 | 3.55 | | |
| esa040u | 7.33 | 4.24 | 4.16 | 11.50 |
| esa041u | 3.79 | 2.13 | 4.28 | |
| esa042u | 2.91 | 4.44 | | |
| esa043u | 1.56 | 3.64 | | |
| esa0447/16u | 1.48 | 3.33 | 3.36 | |
| esa0447/21u | 1.33 | 3.71 | | |
| esa045u | 0.71 | 3.24 | | 12.30 |
| esa046u | 0.71 | 6.69 | | 17.80 |
| esa047u | 0.64 | 1.81 | | |
| esa048u | 0.61 | | 2.58 | |
| esa049u | 0.57 | 3.29 | | |
| esa050u | 0.45 | 2.50 | | |
| esa051u | 0.36 | 4.11 | | |
| esa011u | 0.18 | 2.50 | | |

RESULTS

Free levels of 8OH2'dG in pg/ml were 1.61 (normal case), 2.42 (precursor cell case) 10.8–17.4 (dysplasia cases n=3) and 635.5 (cervical cancer case). The values corrected for dilution by various measures of total protein, amino acids or cell count, indicate initial concentrations in the extracellular cervical environment of ca 80–110,000 pg/ml or ~1000 times the normal plasma levels of 10 pg/ml. This supports the hypothesis that the cervix is in a biochemically isolated area. Ratios of 8OH2'dG/2'dG in the DNA of exfoliated cells were only elevated by factors of 2.1 and 4.8 in the Dysplasia and cancer cases respectively vs. the normal. This also supports the hypothesis that the effect of increase in both DNA damage and repair is magnified in the extracellular matrix in the cervix environment.

It is also consistent with the intuitively less probable hypothesis that the DNA damage and repair is proceeding at a 20–100 fold higher rate in the cervix. A weak correlation ($r=0.431$), driven by high values in the cancer patients between urinary and cervical levels, is also consistent. In the cases with repeat cervical samples, the values were consistent within an individual. Urinary 8OH2'dG values are highly individually specific and the same may hold for the cervix.

The absolute levels of 8OH2'dG based on estimates of the amount of extracellular matrix from protein values in cervico vaginal lavage samples and actual weights of PAP smear samples are on the order of 200–800 pg/ml or ca 20–80 times the levels of 10 pg/ml observed in plasma (2). This supports the hypothesis and necessary diagnostic requirement that the cervix is a semi-isolated in-situ area with respect to transport and excretion of DNA damage products.

The very slight not statistically significant increase in DNA damage products in the DNA itself supports the hypothesis that both damage and repair are up regulated and that the effect is magnified in the extracellular matrix.

While uncorrected 8OH2'dG concentrations are statistically higher in the cancer patients and patients at risk than in controls the use of Tyramine as a normalizer reflecting sample dilution and acquisition factors of the extracellular matrix is effective in compressing the scatter of the data.

Tyramine normalized levels of 8OH2'dG in all control samples and in two cases of findings of Abnormal Squamous Cells of Uncertain Significance (ASCUS) are all below the level of 1.6 pg 8OH2'dG/ng Tyramine. All subjects with identified cervix cancer and two with a high degree of suspicion of cancer are about 16000 pg 8OH2'dG/ng Tyramine. Patients with intermediate possibly precancerous problems and risk factors have 8OH2'dG/Tyramine ratios that are intermediate between control and cancer and may predict an enhanced degree of risk of an early cancer that will manifest subsequently.

The presence of measurable 8OH2'dG phosphate as a significant portion of the total 8OH2'dG occurs in all the cancer cases and in three of the cases with significant risk factors and initial per cancerous indicators.

Chlorotyrosine is found in seven cases and may in the case of ESA051 indicate a significant level of infection as well as or instead of an early cancer lesion.

Thus, the invention and concept provides an index of 8OH2'dG/Tyramine that separates cervical cancer subjects from controls by a minimum factor of 1000 and gives intermediate values for various degrees of risk and findings of abnormal or precancerous cells or lesions. A unique marker of excretion of a portion of 8OH2'dG as the phosphate is found in all cancer subjects and may provide the first indicator of the culmination of risk and insult factors in an early cancer in the individuals with high 8OH2'dG/Tyramine ratios. The ability to commeasure markers of inflammation and infection provides additional diagnostic discrimination between risk factors and actual development of a cancerous lesion.

Several possible candidates for dilution normalizing compounds also were identified from application of a protocol for analysis of the majority of oxidizable compounds in the cervical lavage supernate. Tyramine (TYRA) notably appears to be an attractive normalizer:—it is a uniquely elevated product of cervical cellular metabolism relative to other cellular material (Buccal cells, lymphocytes, alveolar and pharyngeal lavage, brain and muscle dialysates); it is excreted rapidly to the extracellular matrix; and it is co-determinable with 8OH2'dG with the technology employed. For the six test cases, the mole ratios of 8OH2'dGx1000/TYRA were: 1.48 (normal case), 7.34 (precursor cell case), 19.3–22.5 (Dysplasia cases n=3) and 17956 (Cervical cancer case).

Thus, there appears to be a correlative decrease in 8OH2'dG levels with increased coQ10 levels in plasma, or in the local in situ cervical area. Accordingly, the analytical strategy of measuring both free and DNA levels of 8OH2'dG in conjunction with the coQ10 also provides a basis for discriminating between changes in the rate of oxidative damage and changes in the rate of repair associated with the coQ10 levels.

The invention is susceptible to modification. For example, analysis of stool samples for the presence and level of 8OH2'dG and 8OH2'dG phosphates (which typically do not occur above about 0.1 pg/gm in normal feces) both as timed or total output and normalized against levels of the tyrosine metabolite gentisic acid may be employed as a diagnostic of colon or lower bowel cancer; analysis of saliva for elevated levels of 8OH2'dG may be employed to provide an early test for esophageal or throat cancer; analysis of urine or semen for elevated levels of 8OH2'dG may be employed to provide an early test for bladder or testicular cancer; pharyngeal or nasal swab, alveolar or bronchial lavage samples for analysis of 8OH2'dG normalized against levels of 4-Hydroxy Phenyl lactic acid may be employed as a diagnostic of pharyngeal, nasal, bronchial or lung cancer respectively; analysis of foliated urithelial cells in timed culture for 8OH2'dG levels normalized against cell number or weight may be employed for diagnosis of bladder or prostate cancer; analysis of menstrual blood for 8OH2'dG leads may be employed for early detection of ovarian cancer; analysis of phlegm for elevated levels of 8OH2'dG may be employed to provide an early test for lung cancer; and analysis of throat swabs may be employed to provide an early test for throat or esophageal cancer.

While not wishing to be bound by theory, it is believed that 8OH2'dG free level measurements represent the combined effect of the rate of DNA damage and repair caused by disease conditions or environmental insults in a living organism. Essentially, it is believed that the whole body rate of production of 8OH2'dG is:

(a) constant in an individual over time in the absence of disease or environmental insult;
(b) genetically determined;
(c) not related to whole body rate of Hydroxyl radical production;
(d) increased by environmental insult from putative DNA adducts (e.g. pyrenes, Toluidine Arsenic, etc.);
(e) increased in several neurodegenerative diseases;
(f) assessed equally well by spot and 24 hour urines;
(g) not affected by antioxidants tocopherol and ascorbate; and
(h) not affected by diet and converted (via HCl and glycolase) to 8OH2'dGua in the stomach.

The clearance rate from cells and the body as a whole is believed to be very rapid. Normally clearance is via urine but also may be by saliva and sweat. If rates are accounted for there are compartmental correlations among plasma and urine and saliva and DNA damage levels in leucocytes. Typically, ca. 30% of the whole body 8OH2'dG output is from the brain.

Compartmental correlations can be used to determine specific organ involvement. For example, in C. Elegans culture there are bursts of production during rapid mitosis. Isolated Mitochondrial preparations also produce 8OH2'dG in respiration. The relationships among different adducts are different in rapid mitosis, stable cell number cultures and mitochondrial cultures. Levels in DNA are only weakly correlated with rate of production.

Physiologically or transport isolated reservoirs concentrate the products and magnify the effects of DNA damage and repair, e.g. although I have measured only an 11% increase in urine levels of smokers, I have measured a 400% increase in pharangeal swab samples.

Thus, it is believed that rates of DNA damage are primarily affected by: (a) factors causing changes in the conformation of the DNA (mitosis, binding of endogenous and exogenous adducts, transcription); and (b) increases in free radical production in subcellular structures in close dimensional proximity to the DNA (lipid bilayer, nuclear cytosol). The damage and excision product profiles differ for mitochondrial and nuclear DNA and by mechanism of damage. These observations are for cervical cancer, but they are believed equally generalized to lung, lower bowel/colon, prostate, bladder cancer, etc. as follows:

1. The cervix and the extracellular matrix of the cervix is an in situ semi-isolated physiological area with respect to transport of excreted cellular metabolites.

2. The product 8OH2'dG of the combined process of DNA damage and repair is concentrated in the extracellular matrix of the cervix and magnify and reflect the effect of these processes more than the levels of the damage products remaining in the DNA.

3. Correlative or normalizing markers for control of sample dilution and acquisition effects can be selected from metabolites that are (a) not affected by free radical processes, (b) excreted from the cells at a rapid rate, or (c) unique or predominant to the metabolism of cervical cells.

4. The rate of production of DNA damage/repair products will be increased when the cells in the cervix are (a) undergoing rapid division, (b) exposed locally to increased free radical insult as from infection or inflammation, (c) exposed to increased levels of DNA conformation modifying adducts from endogenous processes (metabolic shifts) or exogenous sources (bacterial, or viral infections and/or environmental toxins).

5. The combination of the factors increasing the rate of DNA damage will constitute a risk factor for cancer which will be reflected in higher levels of DNA damage and repair product 8OH2'dG in the extracellular matrix.

6. The magnitude of the different mechanisms of DNA damage will differ and rapid cell division will predominate. Thus, rates of DNA damage in cancer cases and extracellular levels of 8OH2'dG will be significantly higher than in cases of ASCUS or with dysplasia or other risk factors.

7. The relative levels of DNA damage and repair products will differ for different mechanisms. Cancer cells will excrete a significant portion of the endonuclease excised 8OH2'dG as the phosphate or monophosphate, and excise a higher proportion of the damaged base by glycolase excision resulting in elevated levels of 8OH2'dGua in the extracellular matrix. Cancer cells will also preferentially excrete elevated levels of 5-Oxocytidine and reduced levels of 8-nitro guanine.

8. The absolute and relative levels of 8OH2'dG, 8OH2'dG Phosphates, 8OH2'dGua, 8 nitroguanine and 5 Oxocytidine will constitute a profile indicating the presence of cancer independent of the cytological results of the PAP smear and levels of risk factors.

9. The absolute and relative levels of DNA damage products will provide an early indication of cells that are in a precancerous state.

10. Co-determined markers of other free radical damage products will serve to further differentiate the nature of and extent of damage from other risk factors to the rate of DNA damage. Notably chlorotyrosine will serve as an indicator of the effect of inflammation or infection and nitrotyrosine as a normalizer for peroxynitrite DNA damage processes.

It is thus seen that:

1. The levels of 8OH2'dG in cervical vaginal lavage normalized by protein or in PAP smear samples from controls normalized by weight are ca 250–500 pg/ml of extracellular matrix or ca 25–50 times plasma. This is in contrast to the free extracellular levels in muscle, brain, liver, etc. which are on the order of ca 1–3 pg/ml. Therefore, the cervix is seen as semi-isolated with respect to metabolite transport. In cancer cases where the levels of 8OH2'dG in the extracellular matrix are ca 100 times higher than in controls the levels in DNA from the exfoliated cells are only increased by 35% and the difference is not statistically significant. So the concentration of the products in the semi-isolated area magnifies the effect of the DNA damage rate.

2. Using pattern generating techniques to compare cell extracts and extracellular matrix from CVL, PAP smear, buccal cell and alveolar lavage samples and also plasma, red blood cells and urine, the following has been observed:

In CVL and PAP smear samples 23 candidate peaks were over 10× more concentrated in the extracellular matrix, 3 where highly elevated or unique in the CVL/PAP smear samples over all other types. Tyramine was identified as one of these which should be minimally affected by free radical processes and was selected as a sample acquisition normalizer. Note on an operational basis these studies also served to provide acceptable levels of sample quality indicators, e.g. uric acid for urine-contamination and glutathione for blood inclusion.

3. The ratio of 8OH2'dG/tyramine seems to indicate that the rate of damage is higher with cancer and with various risk factors which may include HPV infection, other STD's, multiple partners, hisuitism, endocrine abnormalities, and various equivocal findings from colposcopy.

4. There appears to be a gradation in the increase in rate of DNA damage that is generally in the same direction as increase in risk factors.

5. Even if any of the assumptions are wrong, the rates of local DNA damage in the cervix in the cancer cohort is much higher than in the controls or at risk cohort. Thus, a viable cancer screening test subsists.

6. Some 8OH2'dG phosphate is always seen in cancer. Thus, when it is seen in subjects with high rates of DNA damage and other risk factors it is likely that they actually do have cancer, but it just hasn't advanced to a point where it can be conventionally detected yet. The 8OH2'dGua/ 8OH2'dG ratio was 20 fold higher in two cancer patients than in 8 controls and an algorithm based on ratio and absolute level separates the categories by a factor of 20,000.

The invention is susceptible to modification. For example, the above technique may be employed to assay free levels of the primary oxidative DNA excision product 8-hydroxy-2'-deoxyguanosine (8OH2'dG) and sample normalizing compounds in pharyngeal swabs, induced sputum, bronchial and alveolar lavage using carbon column switching liquid chromatography electrochemical detection (LCEC) as above described. Preliminary work shows three fold elevations of 8OH2'dG in sputum and pharyngeal swabs in smokers. The absolute levels of 8OH2'dG are 10–30 times greater than in plasma which supports an initial hypothesis that the respiratory tract is a semi-isolated physiological transport limited area in which the process of DNA damage and repair will be magnified. In the cervix, a similarly semi-isolated physiological area, cancer patients shown 2000–10000 fold elevations of 8OH2'dG over controls. Thus, there is provided a diagnostic or risk assessment biochemical test for respiratory lesions.

As before, and while not wishing to be bound by theory, the overall hypotheses is that:

1. The respiratory tract is a semi-isolated physiologically transport limited area in which the effects of DNA lesion repair will be magnified.

2. Increased DNA damage will be coupled with up regulated repair and thus the free levels of repair products in the extracellular matrix of the respiratory tract and thus will be more indicative of risk or presence of disease than the levels in the DNA itself.

3. The levels and nature of DNA and RS damage products will differ among processes of DNA ligand formation, increased reactive species product, inflammation/infection and rapid cell mitosis, necrosis and apoptosis and thus provide a route to diagnosis or risk assessment.

The assay of 8OH2'dG and potential sample normalizers in pharyngeal swabs, induced sputum and bronchial alveolar lavage samples, urine, plasma and leukocytes from cohorts of controls, individuals with various risk factors and individuals with respiratory tract lesions using existing technologies permits the determination of the correlations and compartmental relationships among the different sample types and the different diagnostic categories for 8OH2'dG and sample normalizers. This in turn permits evaluation of correlative and process relevant reactive species markers: 8-Hydroxyguanine, 8-Hydroxyguanosine (glycolase excision and RNA damage markers); 7-Methyl guanine (DNA methylation marker); 3-Nitrotyrosine and 8-Nitroguanine (peripheral and DNA reactive nitrogen markers) and 3-Chlorotyrosine (infection or inflammation marker).

The invention also provides strong evidence for concurrent methylation increases in N methyl and NNdimethyl Serotonin (NM5HT NNM5HT) and 7Nmethyl Guanine (7 MG) in plasma and CSF and reduction in the oxidative DNA damage marker 8-Hydroxy 2'Deoxyguanosine (8OH2'dG) in stroke and ischemia in humans. More particularly employing the analysis techniques of the present invention shows a reduction in CNS production of the oxidative DNA damage product 8-Hydroxy-2'-deoxyguanosine (8OH2'dG) and an increase in the production of methylated compounds in a cohort of stroke patients and a similar reduction of 8OH2'dG levels in animal stroke models. Thus, elucidation of the biochemical mechanisms of methylation and oxidative free radical damage to DNA and other cellular structures in stroke and related disorders, and the determination of the relationships of the biochemistry to stroke management, provides a rapid single assay technology for methylated, reactive oxygen and nitrogen species (ROS, RNS) markers in clinically accessible samples and samples relevant to mechanistic studies in animal models. This provides for clinical management of and the evaluation of pharmacological intervention in stroke.

and progressive with time in Amyotrophic Lateral Sclerosis (ALS) (urine plasma and CSF) but not in myopathies. Secondary evidence from the patterns of chromatograms determining 8OH2'dG indicate differences in unidentified purine adducts in urine plasma and CSF among the neurodegenerative disorder (NDD) categories. Again, while not wishing to be bound by theory, the overall hypothesis is as follows:

1. DNA damage products resulting from processes of methylation/ROS/RNS/RCLS are different among controls and NDD.
2. Ligand of endogenous/exogenous compounds with DNA play a role in increased DNA damage.
3. Excision and repair processes differ among controls and NDD.
4. The sites of attack of RS on DNA differ among controls and NDD.

As mentioned supra, other DNA and RNA damage markers and free radical markers may be assayed as indicators for the presence of or risk of various health disorders.

Table IV below lists preliminary conditions developed for DNA damage markers and free radical markers established for the purpose of establishing approximate levels of the analytes of interest. Urine, plasma and cervical extracellular matrix values are presented for pooled control samples. The basic sensitivity of all procedures is from 10–50 pg/ml (500–2500 fg on column).

TABLE IV

| A | B/D | C1/C2 | G1/G2 | pg/ml Plasma | ug/gm creatinine Urine | pg/gm Cervical |
|---|---|---|---|---|---|---|
| 8 OH2'dG | | | | 10.3 | 3.86 | 200 |
| O6MG | 20% MEOH(B1) | 6% An(B2) ADN | 1/1 | A/B | 0.5 | 0.32 | 44 |
| 2'dG/7 MG | 10% MEOH 3% An(B1) | 7% An(B2) ADN | 2/1 | A/B | 500/3 | ND/0.6 | 2000/15 |
| 8 OHG | 1% MEOH(B1) | 1% An(B2) ADN | 1/1 | B/B | 26 | 9.83 | 80 |
| 8 NG | 25% MEOH 4% AN(B2) | 18% An(B1) NBA | 1/1 | A/B | ND | ND | (?) |
| 8 OH2'dA | 8% MEOH(B1) | 4% An(B2) DD | 2/1 | A/A | ND | 0.60 | 30 |
| 5 OH2'dCy | 1% MEOH(B3) | 1% An(B2) ADN | 1/1 | B/C | ND | ND | 30 |
| 5 OHU | 1% MEOH(B3) | 1% An(B3) ADN | 1/1 | B/C | ND | 0.40 | 56 |
| 3 NT/3 CIT | 10% MEOH 3% AN(B1) | 7% An(B1) NBA | 2/1 | B/B | 3.7/1.1 | ND | 20/10 |

MEOH - methanol An - acetonitrile;
B1 - lithium acetate 0.1 M pH 6;
B2 - lithium phosphate 0.1 M pH 3;
B3 - pentone sulfonic acid 0.1 M pH 4;
Column Types: 1 - Tosobaas C18 ODS 80 TM;
2 - YMC C8 Y02H1 carbon column;
A - 4.6 mm d × 4.6 mm;
B - 4.6 mm d × 8 mm;
C - 4.6 mm d × 13 mm;
ADN - adenosine;
DD - dodecane;
NBA - nitrobenzoic acid;
ND - not detected Preliminary work with purine specific carbon column switching techniques as above described also demonstrates elevations of the DNA hydroxy radical damage marker 8-hydroxy-2'-deoxyguanosine in a number of neurodegenerative diseases (NDD). Progressive increases with disease have been shown in, e.g. amyotrophic laterial sclerosis. That is to say, preliminary work with carbon column switching LCEC technology in accordance with the present invention has shown that the ROS DNA damage marker 8-hydroxy-2'deoxyguanosine (8OH2'dG) is elevated in Parkinson's Disease (PD) (urine, plasma, and CSF), Alzheimer's Disease (AD) (plasma and urine, Huntington's Disease (HD) (urine), Freidrich's Ataxia (FA) (urine plasma) and that it is elevated It is thus seen that the present invention provides an objective reproducible test for cervical cancer and precancer screening, as well as for early detection of various other cancers and other health conditions including heart disease and various degenerative diseases.

The invention claimed is:

1. A method for detecting cervical cancer in a human comprising collecting samples of cellular and extracellular materials from and adjacent the cervix of the body and analyzing said samples for elevated free levels of nucleotide excision products in the extracellular as compared to the cellular material wherein the nucleotide excision products analyzed are selected from the group consisting of 8-hydroxy-2'-deoxyguanosine and O-6-methylgusnin, and wherein increased levels of said nucleotide excision products indicate detection of cervical cancer.

2. The method according to claim 1, wherein the collected samples comprise materials from cervico vaginal lavage, an endocervical swab or brush sample.

3. The method according to claim 1, wherein the collected samples comprise materials from a standard PAP smear, endo cervical swab or brush sample.

4. The method according to claim 1, wherein said analyzing comprises electrochemical analysis.

* * * * *

UNITED STATES PATENT AND TRADEMARK OFFICE
CERTIFICATE OF CORRECTION

PATENT NO. : 7,214,486 B2  Page 1 of 1
APPLICATION NO. : 10/366909
DATED : May 8, 2007
INVENTOR(S) : Matson It is certified that error appears in the above-identified patent and that said Letters Patent is hereby corrected as shown below:

Col. 19, Claim 1, Line 1, "O-6-methylgusnin" should be --O-6-methylguanin--.+

Signed and Sealed this

Twenty-seventh Day of May, 2008

JON W. DUDAS
*Director of the United States Patent and Trademark Office*